US006985082B1

(12) United States Patent
Dutta et al.

(10) Patent No.: US 6,985,082 B1
(45) Date of Patent: Jan. 10, 2006

(54) CARBON MONOXIDE SENSOR AND METHOD OF USE

(75) Inventors: Prabir K. Dutta, Worthington, OH (US); Scott L. Swartz, Columbus, OH (US); Christopher T. Holt, Columbus, OH (US); Ramachandra Rao Revur, Columbus, OH (US)

(73) Assignees: The Ohio State University Reasearch Foundation, Columbus, OH (US); NexTech Materials, Ltd., Worthington, OH (US)

( * ) Notice: Subject to any disclaimer, the term of this patent is extended or adjusted under 35 U.S.C. 154(b) by 0 days.

(21) Appl. No.: 09/903,916

(22) Filed: Jul. 12, 2001

(51) Int. Cl.
*G08B 17/11* (2006.01)
(52) U.S. Cl. ...................... 340/632; 340/633
(58) Field of Classification Search .............. 340/632, 340/633, 634; 73/23.2, 23.31, 31.02, 31.06, 73/23.4, 25.01, 25.05; 422/88, 94, 98; 257/76, 257/77, 252; 250/493.1, 766; 436/134; 204/424, 431; 423/247
See application file for complete search history.

(56) References Cited

U.S. PATENT DOCUMENTS

| | | | |
|---|---|---|---|
| 4,470,829 A | 9/1984 | Hirai et al. | 95/140 |
| 4,783,433 A | 11/1988 | Tajima et al. | 502/74 |
| 4,917,711 A | 4/1990 | Xie et al. | 95/106 |
| 5,147,827 A | 9/1992 | Chino et al. | 437/237 |
| 5,300,271 A | 4/1994 | Golden et al. | 423/247 |
| 5,529,763 A | 6/1996 | Peng et al. | 423/246 |
| 5,656,827 A * | 8/1997 | Kang et al. | 257/76 |
| 5,841,021 A * | 11/1998 | De Castro et al. | 340/633 |
| 6,202,471 B1 * | 3/2001 | Yadav et al. | 73/31.05 |
| 6,311,545 B1 * | 11/2001 | Tamaki et al. | 73/31.06 |
| 6,429,019 B1 * | 8/2002 | Goldstein et al. | 436/134 |
| 6,474,138 B1 * | 11/2002 | Change et al. | 73/25.01 |
| 6,531,704 B2 * | 3/2003 | Yadav et al. | 250/493.1 |

OTHER PUBLICATIONS

US Fuel Cell Council, "Fuel Cell Power for Vehicles", www.usfcc.com, Spring 2001, 28 pp.
Rao, Report: "CO Sensors for Fuel Cell Applications", Mar. 2, 2000, 1-11.
Lee et al., "Removal of CO From Reformate for PEFC Application", Proceedings of the 1998 Fuel Cell Seminar, 1998, 578-581.
Peng et al., "CO Adsorbents Based on the Formation of a Supported Cu ( CO )Cl Complex", Langmuir 1995, 11 534-537.
Nogami et al., "Preparation and Nonlinear Optical Properties of Quantum-Sized CuCl-Doped Silica Glass by the Sol-Gel Process", J. Am. Ceram. Soc. 74, 1991, 238-240.

(Continued)

*Primary Examiner*—Van T. Trieu
(74) *Attorney, Agent, or Firm*—Standley Law Group LLP

(57) ABSTRACT

A sensor and method of use for detection of low levels of carbon monoxide in gas mixtures. The approach is based on the change in an electrical property (for example: resistance) that occurs when carbon monoxide is selectively absorbed by a film of copper chloride (or other metal halides). The electrical property change occurs rapidly with both increasing and decreasing CO contents, varies with the amount of CO from the gas stream, and is insensitive to the presence of hydrogen. To make a sensor using this approach, the metal halide film will deposited onto an alumina substrate with electrodes. The sensor may be maintained at the optimum temperature with a thick film platinum heater deposited onto the opposite face of the substrate. When the sensor is operating at an appropriate (and constant) temperature, the magnitude of the electrical property measured between the interdigital electrodes will provide a measure of the carbon monoxide content of the gas.

32 Claims, 12 Drawing Sheets

OTHER PUBLICATIONS

Oetjen et al., "Performance Data of a Proton Exchange Membrane Fuel Cell Using H2/CO as Fuel Gas", J. Electrochem. Soc., vol. 143, No. 12, Dec. 1996, 3838-3842.

Igarashi et al., "Hydrogen Electro-Oxidation on Platinum Catalysts in the Presence of Trace Carbon Monoxide", Journal of Electroanalytical Chemistry 391 (1995) 119-123.

Scarano et al., "Morphology and CO Adsorptive Properties of CuCl Polycrystalline Films: a SEM and FTIR Study", Surface Science 387 (1997) 236-242.

Matsui et al., "Ionic Conductivity of Cuprous Chloride Containing Cuprous Sulfide", J. Electrochem. Soc.: Solid-State Science and Technology, Apr. 1977, 610-614.

Joshi et al., "Electrochemical Studies on Single Crystalline CuCl Solid Electrolyte" J. Electrochem. Soc.: Electrochemical Science and Technology, vol. 122, No. 8, Aug. 1975, 1071-1080.

Jow et al., "The Effect of Dispersed Alumina Particles on the Electrical Conductivity of Cuprous Chloride", J. Electrochem. Soc.: Solid-State Science and Technology, vol. 126, No. 11, Nov. 1979, 1963-1972.

Hakansson et al., "Preparation and Structural Characterization of Cu (CO) Cl" Inorg. Chem. 1990, 29, 5241-5244.

Ida et al., "The Preparation and Properties of Polycrystals of Solid Electrolyte Ultrafine Particles", Surface Review and Letters, vol. 3, No. 1 (1996) 41-44.

Seguin et al., "Preparation of Thin Films of Copper (I) Bromide by R.F. Sputtering: Morphology and Electrical Properties", Thin Solid Films 323 (1998) 31-36.

Villain et al., "Study of Polycrystalline CuBr and the Interface Cu/CuBr by Impedance Spectroscopy", Solid State Ionics 83 (1996) 191-198.

Sequin et al., "Mixed Ionic-Electronic Conducting Thin-Films of CuBr: A New Active Component for Gas Sensors?", Sensors and Actuators 74 (1999) 237-241.

Lauque et al., "Electrical Properties and Sensor Characteristics for NH3 Gas of Sputtered CuBr Films", Sensors and Actuators B 59 (1999) 216-219.

Lauque et al., "Electrical Properties of Thin-Films of the Mixed Ionic-Electronic Conductor CuBr: Influence of Electrode Metals and Gaseous Ammonia" Journal of European Ceramic Society 19 (1999) 823-826.

Dudfield et al., "Evaluation and Modelling of a CO Selective Oxidation Reactor for Solid Polymer Fuel Cell Automotive Applications", Journal of Power Sources 85 (2000) 237-244.

Rohland et al., "The PEMFC-Integrated CO Oxidation—A Novel Method of Simplifying the Fuel Cell Plant", Journal of Power Sources 84 (1999) 183-186.

Schmidt et al., "Influence of CsCu2Cl3 on the Electrical Conductivity of CuCl", Solid State Ionics 112 (1998) 63-67.

Ida et al., "The Preparation and Properties of Polycrystals of Solid Electrolyte Ultrafine Particles", Surface Review and Letters, vol. 3, No. 1 (1996), 41-44.

Matsui et al., "Ionic Conductivity in Pure and Cadmium-Doped Cuprous Iodide", J. Electrochem. Soc.: Solid-State Science and Technology, Feb. 1977, 300-305.

Chang et al., "The Effect of Particle Size on the Electrical Conductivity of CuCl (Al2O3) Composites" Plasma-Deposited Si3N4, vol. 131, No. 5, May 1984, 1213-1214.

Hsueh et al., "Thermoelectric Power of CuCl Containing CdCl2" The Journal of Chemical Physics, vol. 39, No. 12, Dec. 1963, 3519-3522.

Gurbuz et al., "High-Temperature Tolerant Diamond Diode for Carbon Monoxide Gas Detection", Journal of Applied Physics, vol. 84, No. 12, Dec. 1998, 6935-6936.

Riess et al., "Electrical Conductivity Measurements on Cuprous Bromide, CuBr, in the Presence of Oxygen", Solid State Ionics 59 (1993) 279-286.

Li et al., "High-Temperature Carbon Monoxide Potentiometric Sensor", J. Electrochem. Soc., vol. 140, No. 4, Apr. 1993, 1068-1073.

Brune et al., "The Electrical Conductivity of Single and Polycrystalline Copper (I) Chloride", Materials Research Bulletin, vol. 30, No. 5, 573-579 (1995).

Riess, "Four Point Hebb-Wagner Polarization Method for Determining the Electronic Conductivity in Mixed Ionic-Electronic Conductors", Solid State Ionics 51 (1992) 219-229.

Riess et al., "Failure of Hebb-Wagner Polarization Measurements Due to Decomposition of the Sample", Solid State Ionics 59 (1993) 99-108.

Jiang et al., "A Theoretical Model for Composite Electrolytes-II. Percolation Model for Ionic Conductivity Enhancement", J. Phys. Chem. Solids vol. 56, No. 8, 1113-1124 (1995).

Nakamura et al., Size-Dependent Radiative Decay of Excitons in CuCl Semiconducting Quantum Spheres Embedded in Glasses, The American Physical Society, Physical Review B, vol. 40, No. 12, 8585-8588.

Soga et al., "A Method of Growing CuCl Single Crystals with Flux", J. Electrochem. Soc.: Solid State Science, Apr. 1967, 388-390.

Ekimov et al., "Quantum Size Effect in Semiconductor Microcrystals", Solid State Communications, vol. 56, No. 11, 921-924 (1985).

Maier, "Electrical Sensing of Complex Gaseous Species by Making Use of Acid-Base Properties", Solid State Ionics 62 (1993) 105-111.

Maier, "Defect Chemistry and Conductivity Effects in Heterogeneous Solid Electrolytes", J. Electrochem. Soc.: Solid-State Science and Technology, Jun. 1987, 1524-1535.

Matsui et al., "Inorganic Copper Ion Conductors", Solid Electrlytes 1978, 237-252.

Bhattacharyya et al., "Effective Medium Theory for Ionic Conductivity in Polycrystalline Solid Electrolytes", Solid State Ionics 95 (1997) 283-288.

Maier, "Ionic Conduction in Space Charge Regions", Prog. Solid St. Chem., vol. 23, (1995), 171-263.

Lauer et al., "Conductance Effects of Ammonia on Silver Chloride Boundary Layers", Sensors and Actuators B, 2 (1990) 125-131.

Funke et al., "On the Dynamics of Frenkel Defect Formation and Ionic Hopping in AgCl, AgBr and β-AgI", Solid State Ionics 86-88, (1996) 141-146.

Lauer et al., "Impedance Studies of the Interface Silver Halide/Electronically Conducting Oxide: Detection of an Ionic Space Charge Layer", Solid State Ionics 53-56 (1992) 885-889.

Van Hulle et al., "Space Charge Characteristics of Silver Halide Microcrystals", Phys. Stat. Sol. (a) 44, 229 (1977) 229-236.

Lauer et al., "Impedance Spectroscopic Investigation of the Interface Silver Halide/Oxide: Detection of an Ionic Depletion Layer", J. Electrochem. Soc., vol. 139, No. 5, May 1992, 1472-1479.

Liou et al., "The Ionic Hall Effect in Silver Bromide and Iodide", Journal of Imaging Science, vol. 34, No. 3, May/Jun. 1990, 109-111.

Corish, "Ionic Conductance in the Silver Halides", Journal of Imaging Science, vol. 34, No. 3, May/Jun. 1990, 84-88.

Laskar et al., "Defect Properties and Their Transport in Silver Halides", Journal of Imaging Science, vol. 34, No. 3, May/Jun. 1990, 98-103.

Dudney, "Enhanced Ionic Conduction in Silver Halide-Alumina Composites", Journal of Imaging Science, vol. 34, No. 3, May/Jun. 1990, 104-108.

Lieb et al., "Effect of Ionic Polarizability on Impurity-Vacancy Association in Silver Halides", J. Phys. Chem. Solids, vol. 57, No. 1, 101-107.

Staikov et al., "Effect of Grain Boundaries on the Low-Temperature Ionic Conductivity of Polycrystalline RbAg4I5 and Ag3SBr", Solid State Ionics 93 (1997), 85-93.

Winkes et al., "Surface Resistance Measurements at the Metal/Electrolyte Interface of Ag(100) and Ag(111) Thin Film Electrodes", Surface Science 400 (1998) 44-53.

Maier, "Defect Chemistry and Conductivity Effects in Heterogeneous Solid Electrolytes", J. Electrochem. Soc.: Solid-State Science and Technology, Jun. 1987, 1524-1535.

Friauf, "Determination of Ionic Transport Processed in AgCl and AgBr", Journal De Physique, Tome 38, Septembre 1977, 1077-1088.

Chowdhary et al., "Electrical Conduction in AgI-Al2O3 Composites", J. Electrochem. Soc.: Electrochemical Science and Technology, Jan. 1985, 123-124.

Shahi et al., "Ionic Conductivity and Thermoelectric Power of Pure and Al2O3-Dispersed AgI", J. Electrochem. Soc.: Electrochemical Science and Technology, vol. 128, No. 1, Jan. 1981, 6-13.

Liou et al., "Ionic Hall Effect in Crystals: Independent Versus Cooperative Hopping in AgBr and α-AgI", The American Physical Society, Physical Review B, vol. 41, No. 15, May 1990, 10481-10485.

Kaneda et al., "Hall Effect of Silver Ions in RbAg4I5 Single Crystals", Physical Review Letters, vol. 29, No. 14, Oct. 1972, 937-939.

Knotek et al., "The Absence of a Measurable Hall Effect in the Superionic Conductor RbAg4I5", Solid State Communications, vol. 21, 1977, 625-627.

Newman et al., "The Ionic Hall Effect in the Solid Electrolyte C5H6Nag5I6", Electrochemica Acta, vol. 22, 1977, 811-814.

* cited by examiner

CARBON MONOXIDE SENSOR AND METHOD OF USE

The present invention was made with Government support under Grant No. DE-FG02-99ER 86099 awarded by the U.S. Department of Energy. The United States Government may have certain rights to this invention under 35 U.S.C. §200 et seq.

TECHNICAL FIELD OF THE INVENTION

This invention relates to a sensor that is capable of detecting low concentrations of carbon monoxide (CO) in a relatively hydrogen-rich and relatively oxygen-free gas mixture. The sensor can be used within a wide variety of systems presenting this type of environment, such as fuel processors for PEM fuel cell power generation systems that are being developed for automotive, residential, and other applications.

BACKGROUND OF THE INVENTION

Fuel cells are being developed as power sources for many applications. Fuel cells generate power, without combustion, by extracting the chemical energy of hydrogen from hydrogen containing fuels. Advantages of fuel cells include high efficiency and very low release of polluting gases (e.g., $NO_x$) into the atmosphere. Of the various types of fuel cells, the proton exchange membrane (PEM) fuel cell is receiving considerable attention for transportation applications due to its low weight, low temperature operation, and its considerable potential for mobile and residential applications. The heart of the PEM fuel cell is a membrane electrode assembly (MEA), which is a sheet of a proton-conducting polymeric material (e.g., Nafion) with thin coatings of platinum containing electrocatalysts (anodes and cathodes) on opposite faces. Several MEAs are stacked with interposed electrically conductive elements (current collectors) that contain appropriate channels for distributing the gaseous reactants over the surfaces of the anode and cathodes. PEM fuel cells operate most efficiently when hydrogen is the anode reactant (fuel) and oxygen as the cathode reactant (oxidant). However, for more practical applications, air is used as the oxidant and a hydrogen rich gas (derived from hydrocarbons) is used as the fuel. For transportation applications, the use of liquid hydrocarbon fuels for fuel cells, such as gasoline, is most attractive due to transportability, high energy density, and existing infrastructure.

One of the problems of using hydrocarbons to produce the hydrogen required for operating the PEM fuel cell is that carbon monoxide is a poison to the platinum electrocatalysts in the anode of the MEA. Performance of the PEM fuel cell can be degraded when CO is present at levels as low as 20 parts per million, and considerable performance degradation is observed when the CO content is higher than 100 parts per million. Thus, the hydrocarbon fuels must be converted into a hydrogen rich gas containing little or no carbon monoxide (since trace amounts of CO will degrade PEM fuel cell performance). Fuel processors, utilizing multiple catalytic reactor stages, are being developed to meet this requirement. For the automotive application, especially, it will be imperative to have a sensor that monitors the amount of carbon monoxide at various stages of the fuel processing system, and to monitor CO content of the hydrogen-rich gas exiting the fuel processor.

The importance of carbon monoxide sensors for automotive PEM fuel cell systems is illustrated by a schematic of an automotive fuel processor, shown in FIG. 1. Fuel processing 10 typically involves three or four catalytic stages. The first reforming step 14 involves the reaction of gasified hydrocarbons 12 with air 11 (partial oxidation or POX), or with air 11 and steam 13 (autothermal reforming or ATR), to convert gasoline, methanol or other hydrocarbons into a gas mixture rich in hydrogen and carbon monoxide. This reformed gas mixture then is subjected to the water-gas-shift reaction ($CO+H_2O \rightarrow CO_2+H_2$) to reduce carbon monoxide levels and increase hydrogen content. The water-gas-shift (WGS) reaction is usually performed in two separate reactions, the first 15 at relatively high temperature (to convert most of the carbon monoxide), and the second 16 at a lower temperature (where equilibrium CO contents are lower). After exiting the WGS reactors 15 and 16, the hydrogen-rich reformate gas enters the preferential oxidation (PROX) reactor 17 where the gas is mixed with air 11 to oxidize remaining carbon monoxide to carbon dioxide. A key technical challenge facing developers of fuel processors for automotive applications is the requirement to maintain low carbon monoxide contents during operational transients, such as those that would occur during acceleration and deceleration. Transients can cause spikes in the carbon monoxide content of the reformed gas. The primary use for the CO sensors under development in this program is to measure the CO content of the reformate gas 18 exiting the PROX reactor 17. There are two potential benefits of this type of CO sensor:

(1) The sensor can provide feedback to the PROX reactor. This will allow the optimum amount of air to be fed into the PROX reactor (and minimize any wasted hydrogen); and
(2) The sensor will protect the PEM fuel cell stack. When a high CO content is detected the reformate gas would be diverted from the stack (with power being provided by a battery) until the CO level returns to tolerable levels.

Existing carbon monoxide sensors cannot meet the requirements of the fuel cell application. Commercial CO sensors, typically based on semiconducting oxides (e.g., tin oxide), operate on the basis of a resistance change due to oxidation of CO to $CO_2$ (carbon dioxide). This type of sensor cannot work for the fuel cell application because of the absence of oxygen in the reformate gas. Further, even if oxygen were available, it would be difficult for the tin oxide sensor to detect low levels of carbon monoxide in the presence of a high concentration of hydrogen (because oxidation of hydrogen also will occur). With current technology, optical sensors are the only current option for rapid and accurate detection of CO in a hydrogen-rich atmosphere. However, optical sensors are bulky and extremely expensive, and it is doubtful that the size and cost of these systems can be reduced sufficiently for the fuel cell application.

It is therefore a goal of the present invention to provide a sensor that can detect carbon monoxide in a hydrogen-rich oxygen-deficient environment. That is to say, it is an object of the present invention to provide a sensor that can detect carbon monoxide in a reducing environment. It is a further goal of the present invention to provide a sensor that can detect carbon monoxide in a hydrogen-rich gas stream so as not to poison the catalyst of a PEM fuel cell.

SUMMARY OF THE INVENTION

The present invention presents a novel approach for detection of low levels of carbon monoxide in hydrogen-rich gas mixtures. The approach is based on the change in electrical resistance that occurs when carbon monoxide is selectively absorbed by a thick film of copper chloride (or other metal halides). The resistance change was shown to occur rapidly with both increasing and decreasing CO contents, to vary with the amount of CO from the gas stream, and was insensitive to the presence of hydrogen. The present invention includes a sensor and methods of using the sensor to measure the concentration of CO in a gas stream.

A sensor for determining the concentration of carbon monoxide in a gas stream as a function of measured resistance of the present invention comprises a non-conductive substrate, having a first and a second side, onto which a first and a second electrode are deposited on the first side such that the first electrode is not in contact with the second electrode. A sensing material is in electrical contact with the first electrode and the second electrode. The sensing material is a metal halide capable of absorbing carbon monoxide from the gas stream and has an electrical resistance that varies in proportion to the absorbed carbon monoxide on the sensing material.

It is preferred that sensors of the present invention employ alumina substrates. However, it should be noted that any non-conductive suitable material may be used for the substrate. Additionally, it is preferred that the first and the second electrode are interdigital electrodes disposed so as not to touch one another. It is preferred that the first and second electrodes are made of gold or copper. Further, it is preferred that the sensing material is comprised of a majority of cuprous chloride (CuCl) and a minority of a copper halide wherein the copper of the copper halide has a valence of at least +2. It is most preferred that the sensing material is cuprous chloride. It is preferred that sensors of the present invention further comprise a heater deposited on the second side of the substrate and adapted to maintain the sensor at a substantially constant temperature. It is most preferred that the heater is a platinum heater. Additional methods of temperature control may be employed to assist the heater in maintaining a constant sensor temperature such as computer control or other known methods. With respect to sensors of the present invention based upon copper, these sensors operate best when they are used in a substantially water-free environment. It is most preferred that copper-based sensors of the present invention are used in a water-free environment. In cases where the function of copper-based sensors is adversely affected by exposure to water, it has been found that function may be restored by removal of the water.

A method for using a sensor of the present invention to determine the concentration of carbon monoxide in a gas stream begins by passing a gas stream to a sensor (as described above) with a potential impressed across the first electrode and the second electrode. A measurement may then be taken of the resistance of the sensing material. The resistance of the sensing material is dependent to the concentration of carbon monoxide in the gas stream and may be outputted to a device. It should be noted that a measurement may be taken of any electrical property dependent on the concentration of carbon monoxide in the gas stream. Alternatives to the measuring of resistance include, but are not limited to: conductance and impedance.

In a preferred method of the present invention the device is a display device adapted to provide a read-out of the carbon monoxide concentration based on the measured resistance. It is additionally preferred that the device be a controller adapted to adjust the gas stream in response to the outputted resistance measurement.

A second method for sensing the concentration of carbon monoxide during the conversion of fossil fuel to into a gas stream using a sensor of the present invention comprises the reacting of a flow of gases to produce a gaseous mixture of hydrogen, carbon dioxide, carbon monoxide, nitrogen, and water. The reacted flow of gases is then sent to at least a first reactor adapted to reduce carbon monoxide content and increase hydrogen content, thereby forming a reformate gas. The reformate gas is then sent to at least a second reactor adapted to combine a flow of air with the reformate gas so as to oxidize carbon monoxide to carbon dioxide and so as to not oxidize the hydrogen to water. The oxidized flow of air and reformate gas is then passed to a sensor of the present invention (as described above) where the resistance of the sensing material is measured. The measured resistance is used to provide feedback to the at least second reactor. The resistance of the sensing material provides a measure of the concentration of carbon monoxide in the gas stream and the at least second reactor is adapted to adjust the flow of air in response thereto.

It is preferred that the method additionally comprises the step of directing the oxidized flow of air and reformate gas to a next device. It is more preferred that the method further comprises the step of diverting the oxidized flow of air and reformate gas from the next device when the concentration of carbon monoxide detected by the sensor exceeds a threshold. Suitable next devices may include a PEM fuel cell or storage tank, although other suitable next device may be obvious to one skilled in the art.

BRIEF DESCRIPTION OF THE DRAWINGS

FIG. 1 shows a schematic of an automotive fuel processor that a sensor of the present invention may be used on.

DETAILED DESCRIPTION OF THE PREFERRED EMBODIMENT(S)

A novel approach for detection of low levels of carbon monoxide in hydrogen-rich gas and oxygen-deficient mixtures is provided below. The approach is based on the change in electrical resistance that occurs when carbon monoxide is selectively absorbed by a thick film of copper chloride (or other metal halides). This resistance change was shown to occur rapidly with both increasing and decreasing CO contents, to vary with the amount of CO from the gas stream, and was insensitive to the presence of hydrogen. Hydrogen-rich gas streams contain at least 10% hydrogen ($H_2$). Oxygen-deficient gas streams contain less than 0.5% oxygen ($O_2$).

The gas stream in which the sensor is used has a reducing nature. That is to say, the gas stream contains substantially no oxidizing gases such as oxygen. The gas stream has a reducing nature due to the presence of hydrogen or other reducing gases. For the purposes of this application, hydrogen is representative of a reducing gas and oxygen is representative of an oxidizing gas.

The preferred opera ting temperature of sensors of the present invention is a temperature at or above the gas stream temperature.

Figure 1:
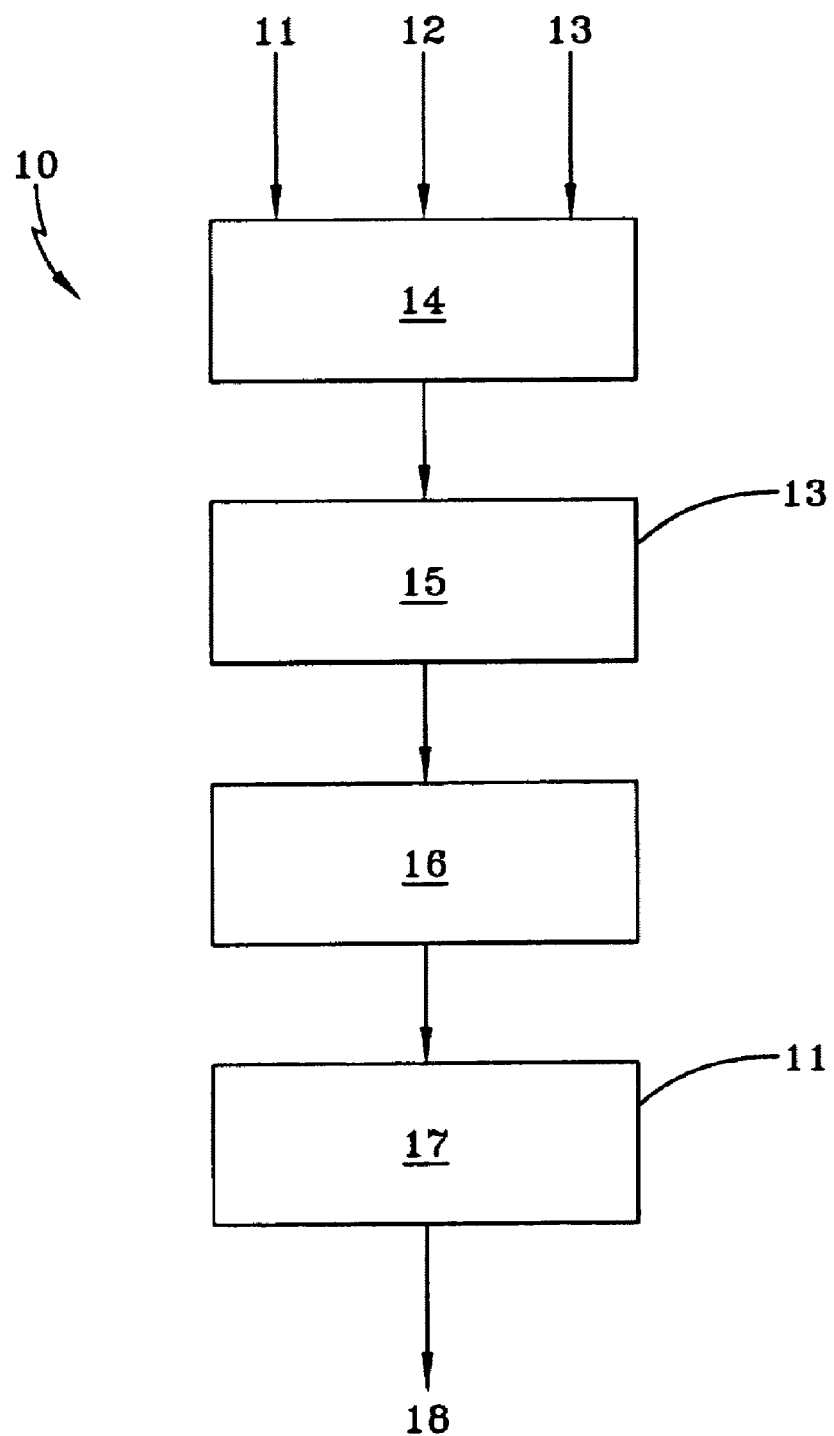
Figure 2:
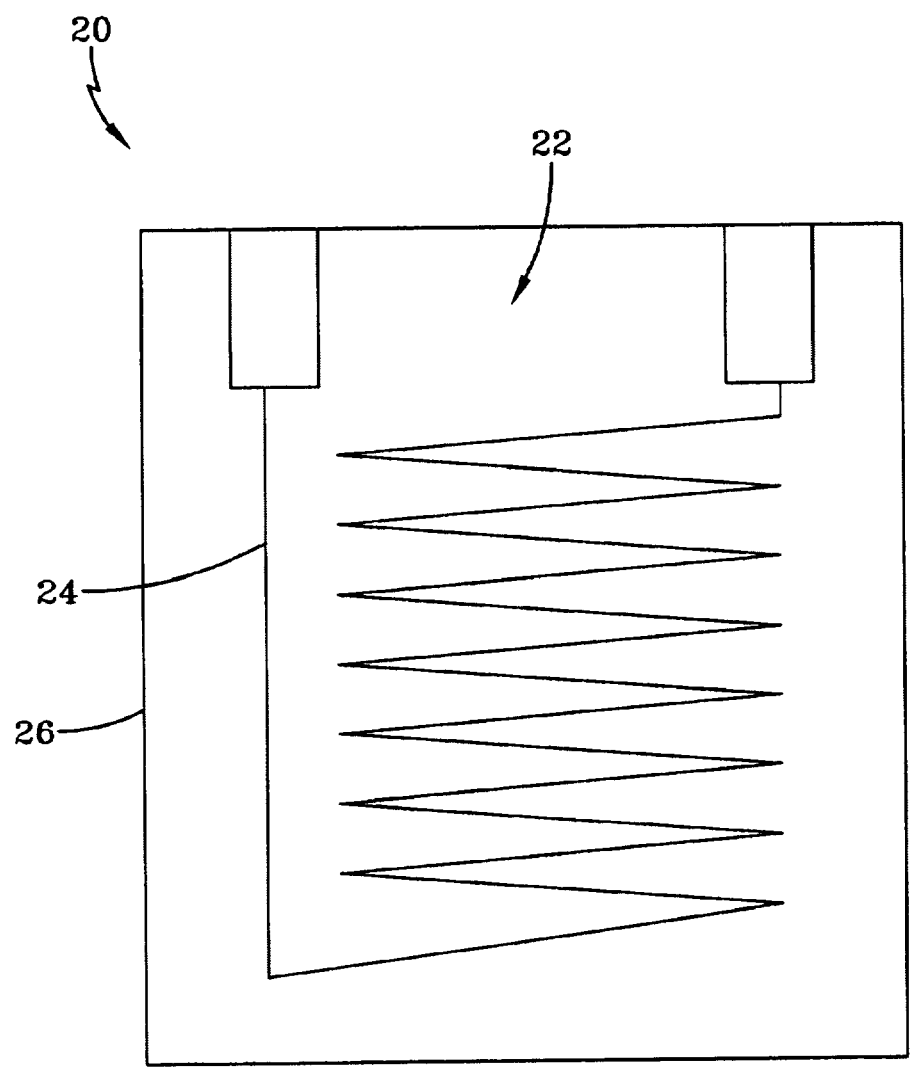
FIG. 2 shows the bottom face of a sensor in accordance with one embodiment of the present invention.
Figure 3:
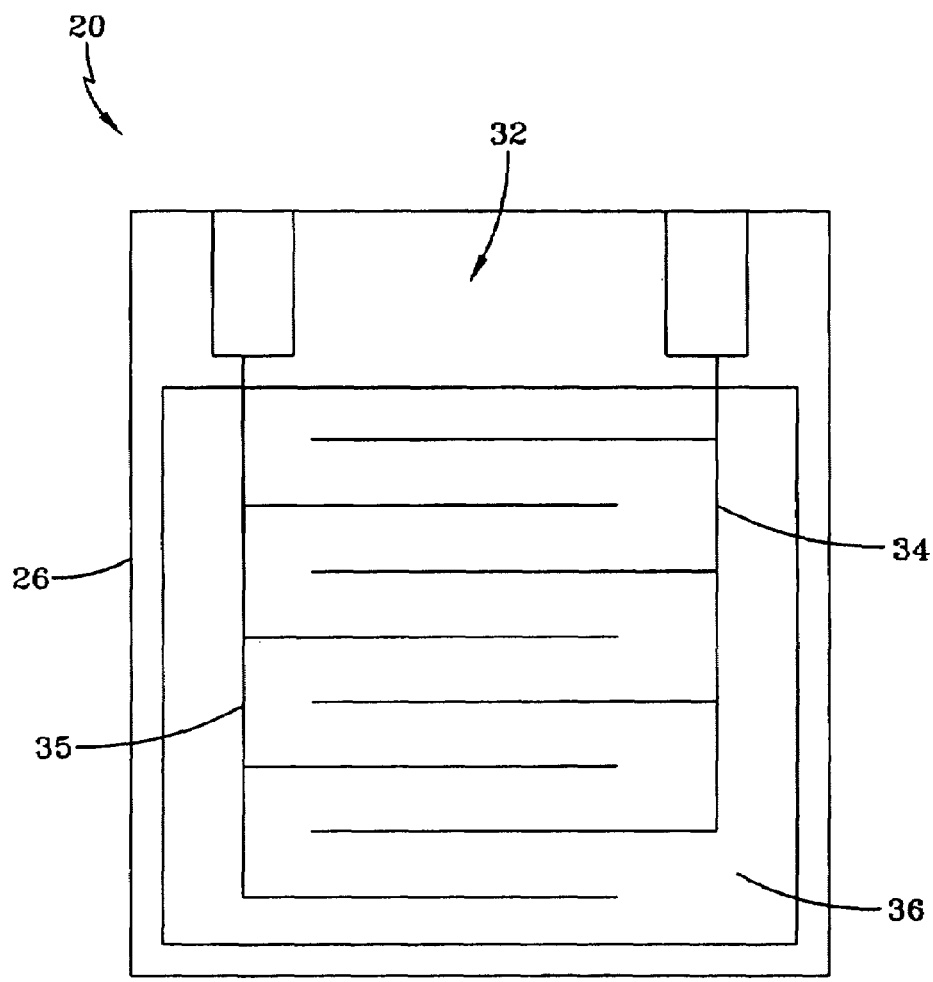
FIG. 3 shows the top face of a sensor in accordance with one embodiment of the preset invention.

Turning to FIGS. 2 and 3, a preferred sensor of the present invention is presented. FIGS. 2 and 3 respectively illustrate the bottom and top faces of a preferred sensor in accordance with one embodiment of the present invention. FIG. 2 details the bottom face 22 of preferred sensor 20. The sensor 20 is preferably constructed from an alumina substrate 26 upon which a thick-film platinum heater 24 is preferably deposited. In addition to alumina, the sensor substrate may be any suitable ceramic or non-conductive material. FIG. 3 shows the top face 32 of sensor 20. The top face 32 of sensor 20 has a first interdigital electrode 34 and a second interdigital electrode 35. The interdigital electrodes, 34 and 35, are preferably constructed of gold. However, the interdigital electrodes, 34 and 35, may be made of copper or any other suitable conducting material. The sensing material 36 is preferably deposited onto the top face 32 of sensor 20 so as to cover an area containing the interdigital electrodes 34. The sensing material 35 is preferably constructed of copper chloride (CuCl) formed by one of the fabrication methods outlined below. However, the sensing material 35 may be formed from any metal halide whose electrical resistance is dependent upon CO adsorption.

The thick-film platinum heater 24 is adapted to supply heat to the sensor 20 to maintain constant temperature. A constant sensor temperature ensures that the output of the sensor is consistent and accurate, as resistance is a function of temperature.

The sensor determines the presence of CO in the gas stream by measuring the resistance between the first interdigital electrode 34 and the second interdigital electrode 35 across the sensing material 36.

FABRICATION PROCESSES

Different fabrication methods were evaluated for preparing copper chloride (CuCl) films. The films were deposited onto alumina substrates with gold IDE electrodes, and the CO sensing performance was evaluated. Varying degrees of copper chloride sensitivities were observed in copper chloride films prepared by the five methods. The best results were obtained with pure copper chloride film prepared by Methods 1 and 2, which are described below:

Method 1: CuCl in Acetonitrile Drop Deposition. With this method, 50 mg of "purified" CuCl was first dissolved in 5 ml of acetonitrile, with nitrogen bubbling through the solution to prevent any aerial oxidation. An IDE substrate was placed on a hot plate and heated to 90° C., a temperature above the boiling point of acetonitrile (82° C.). The CuCl solution was added dropwise to the hot IDE, allowing the acetonitrile to evaporate, leaving a CuCl film. The drops were added until reasonable film thickness was obtained. Two types of CuCl film samples were prepared: films deposited with nitrogen bubbling through the acetdnitrile solution and drying under nitrogen (anaerobic) and films deposited with bubbling nitrogen and drying in air (aerobic). The CuCl films prepared under the anaerobic condition were white (presumably pure copper chloride), whereas films produced under the aerobic condition were grayish-white (presumably due to partial oxidation).

Method 2: CuCl in Acetonitrile Solvent Evaporation Deposition. This method involved the initial preparation of a solution of 75 mg of purified CuCl in 5 ml of acetonitrile, as, described above. An IDE-alumina substrate was placed in a 10-ml beaker and submerged in the CuCl/acetonitrile solution. The beaker was placed in a vacuum oven at room temperature to evaporate the acetonitrile. During the removal of the acetonitrile, the CuCl physically precipitates onto the IDE substrate. The sample was vacuum dried until all solvent was removed. Film samples produced by this method were grayish white, possibly due to film oxidation when the beaker was transferred into the vacuum oven.

Figure 4A:
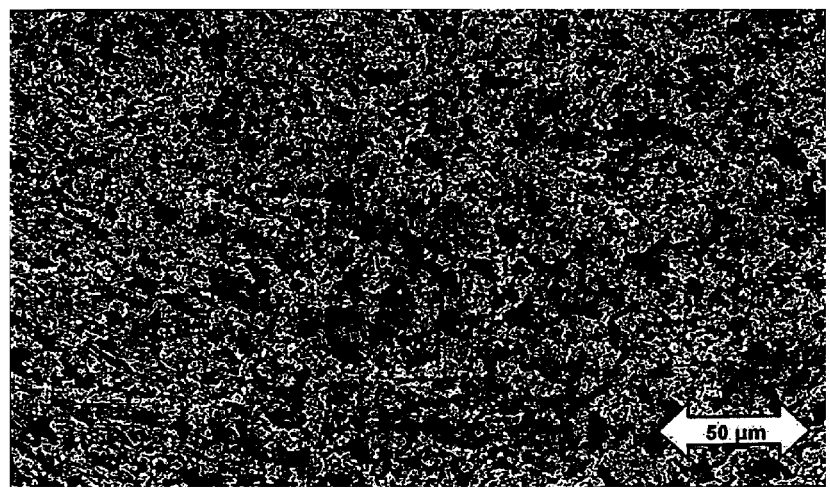
FIG. 4a SEM micrograph of copper chloride film prepared in accordance with one method (Method 1) of the present invention.
Figure 4B:
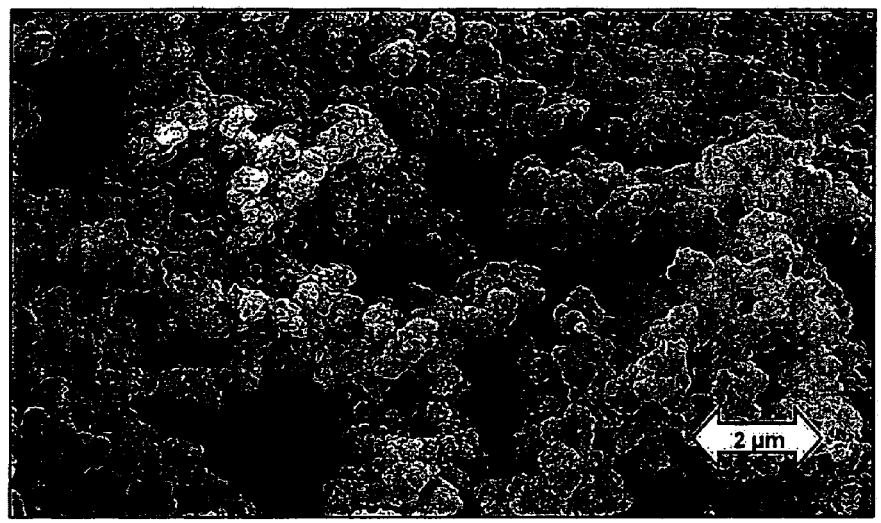
FIG. 4b is a SEM micrograph of copper chloride film prepared in accordance with one method (Method 1) of the present invention.
Figure 4C:
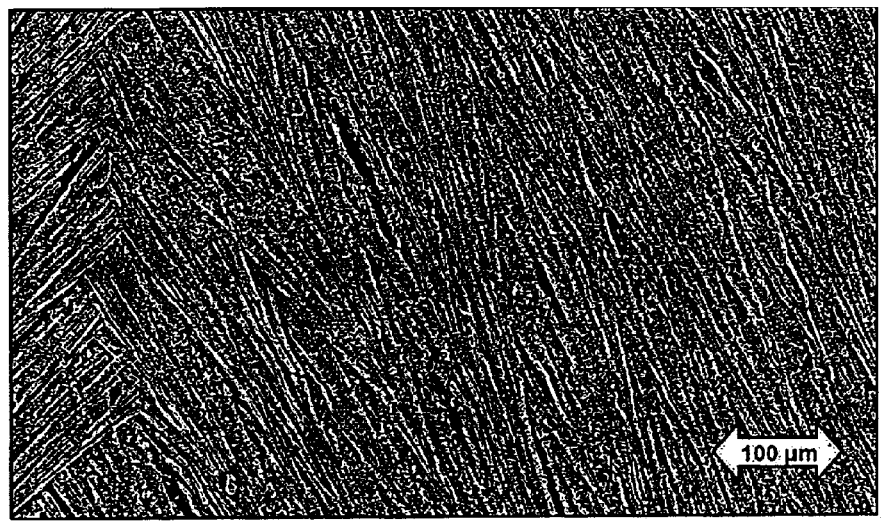
FIG. 4c is a SEM micrograph of copper chloride film prepared in accordance with one method (Method 2) of the present invention.
Figure 4D:
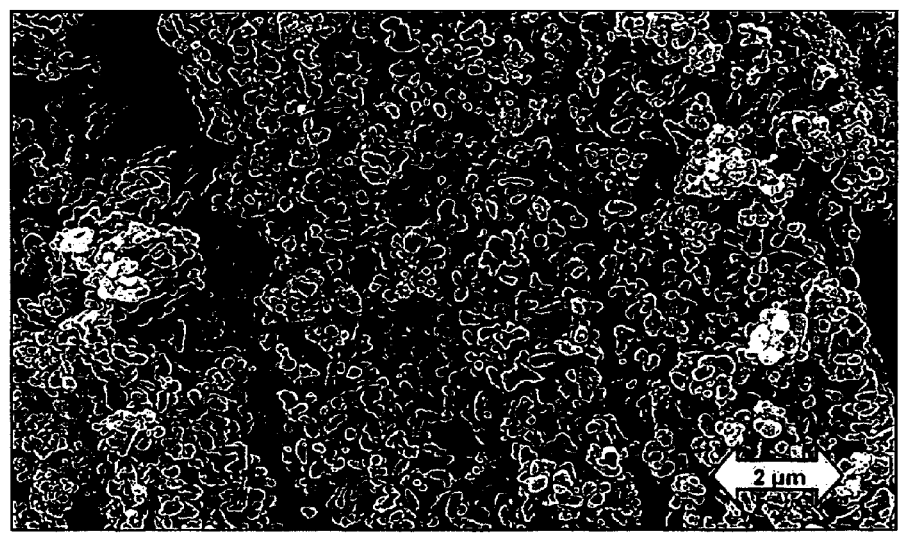
FIG. 4d is a SEM micrograph of copper chloride film prepared in accordance with one method (Method 2) of the present invention.

X-ray diffraction data obtained on copper chloride films prepared by the above methods indicated single-phase copper chloride (CuCl) with the expected nantokite structure. The microstructures of film samples prepared from CuCl/acetonitrile solutions were evaluated by scanning electron microscopy (see FIGS. 4a through 4d). Very striking differences in the morphology of the two samples were observed. The sample prepared by Method 1 (dropwise addition of the acetonitrile solution onto a heated substrate) exhibited a highly porous structure of spherical CuCl particles (see FIGS. 4a and 4b), whereas the film sample produced by Method 2 (direct precipitation of CuCl during evaporation of acetonitrile) exhibited a lamellar structure, with laminae comprised of very small spherical CuCl crystals (see FIGS. 4c and 4d). The CO sensing performance of copper chloride film samples were evaluated. Results of sensor evaluations are described below.

Sensor 1A (Casting from "Anaerobic" CuCl/Acetonitrile Solutions). The CO sensing performance of samples prepared by Method 1 (i.e., drop-wise casting of CuCl/acetonitrile solutions onto heated IDE-alumina substrates) was evaluated for nitrogen and nitrogen/hydrogen gas atmospheres. The first sample that was tested was a CuCl film sample prepared under purely "anaerobic" conditions (i.e., with nitrogen bubbling through the acetonitrile solution during film casting). Before testing, this sample was reduced in hydrogen for two hours at 150° C. This sample exhibited no response whatsoever to CO at 50° C.

Figure 5:
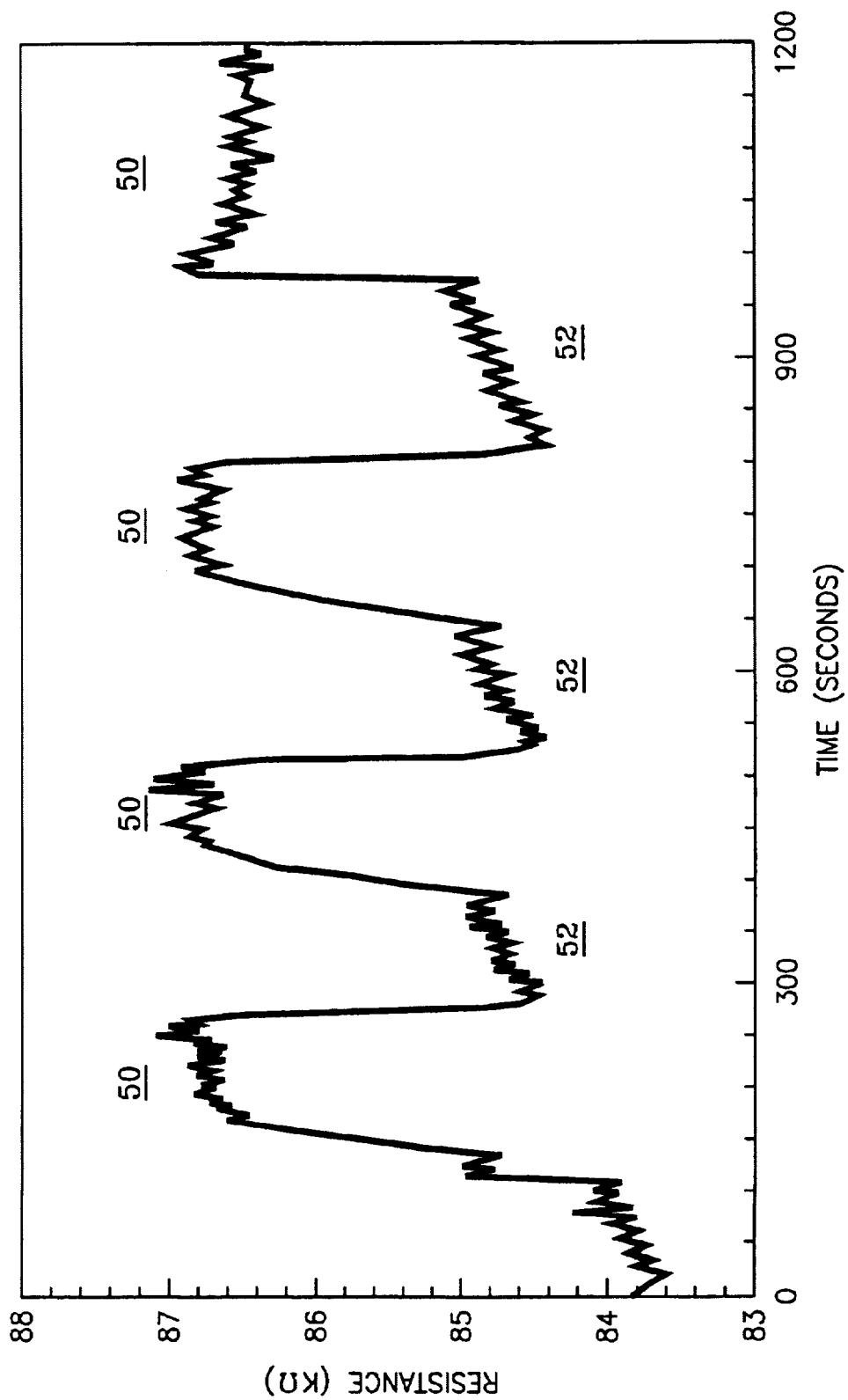
FIG. 5 is a CO sensitivity graph of CuCl film sample of Method 1B at 50° C. in $N_2$.
Figure 6:
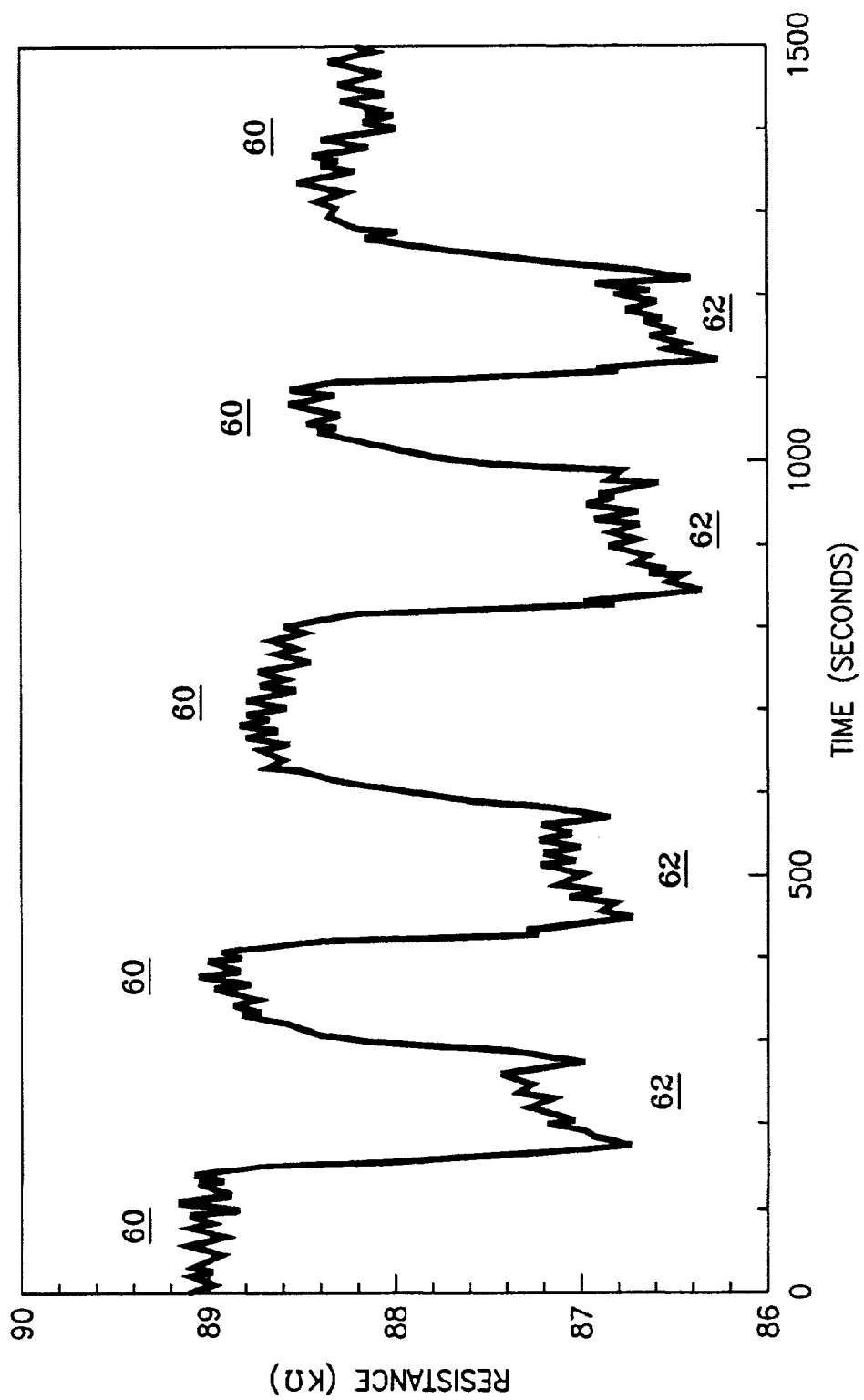
FIG. 6 is a CO sensitivity graph of CuCl film sample of Method 1B at 50° C. in the presence of $H_2$.

Sensor 1B (Casting from "Aerobic" CuCl/Acetonitrile Solutions). A CuCl film sample prepared by Method 1 was prepared under "aerobic" conditions (the film was deposited from an acetonitrile solution and dried in air). This sample also was reduced in hydrogen as described previously. The film sample exhibited strong responses to CO, both in nitrogen and nitrogen/hydrogen atmospheres (see FIGS. 5 and 6). FIG. 5 shows the CO sensitivity of a CuCl film sample of Method 1B at 50° C. in $N_2$. The resistance of a sensor was tracked through periods of pure $N_2$ 50 interrupted by periods of 1000-ppm CO gas 52. FIG. 6 shows the CO sensitivity of CuCl film sample of Method 1B at 50° C. in the presence of $H_2$. The resistance of a sensor was tracked through periods of $N_2/H_2$ 60 interrupted by periods of CO gas 62. The response of the sensor to 1000-ppm CO was stable for many cycles. The hydrogen gas concentration was varied from 0 to 50% and absolutely no change in the baseline resistance or CO sensitivity was observed.

Figure 7:
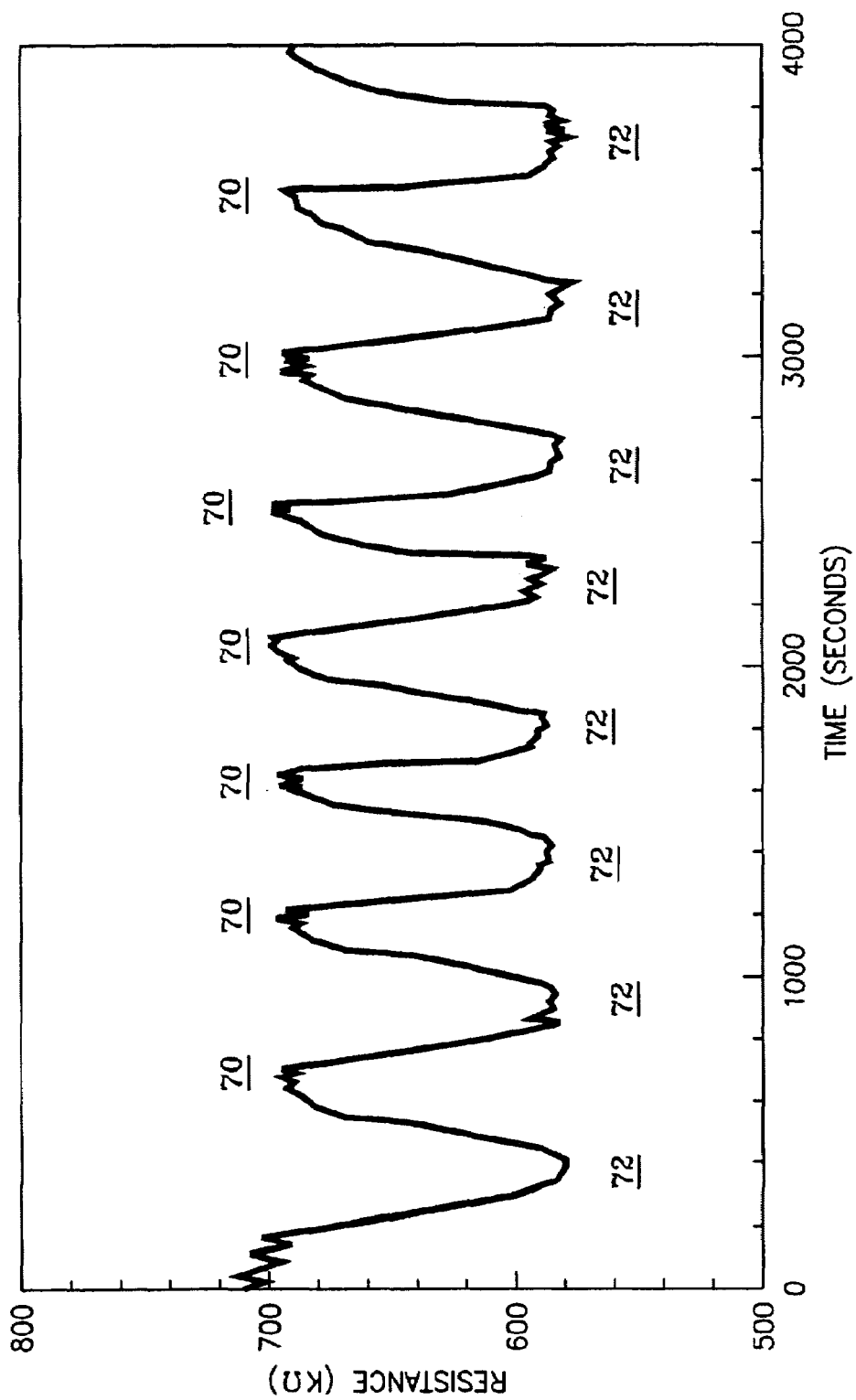
FIG. 7 is a CO sensitivity graph of CuCl film samples of Method 2 at 50° C. in the presence of $H_2$.
Figure 8:
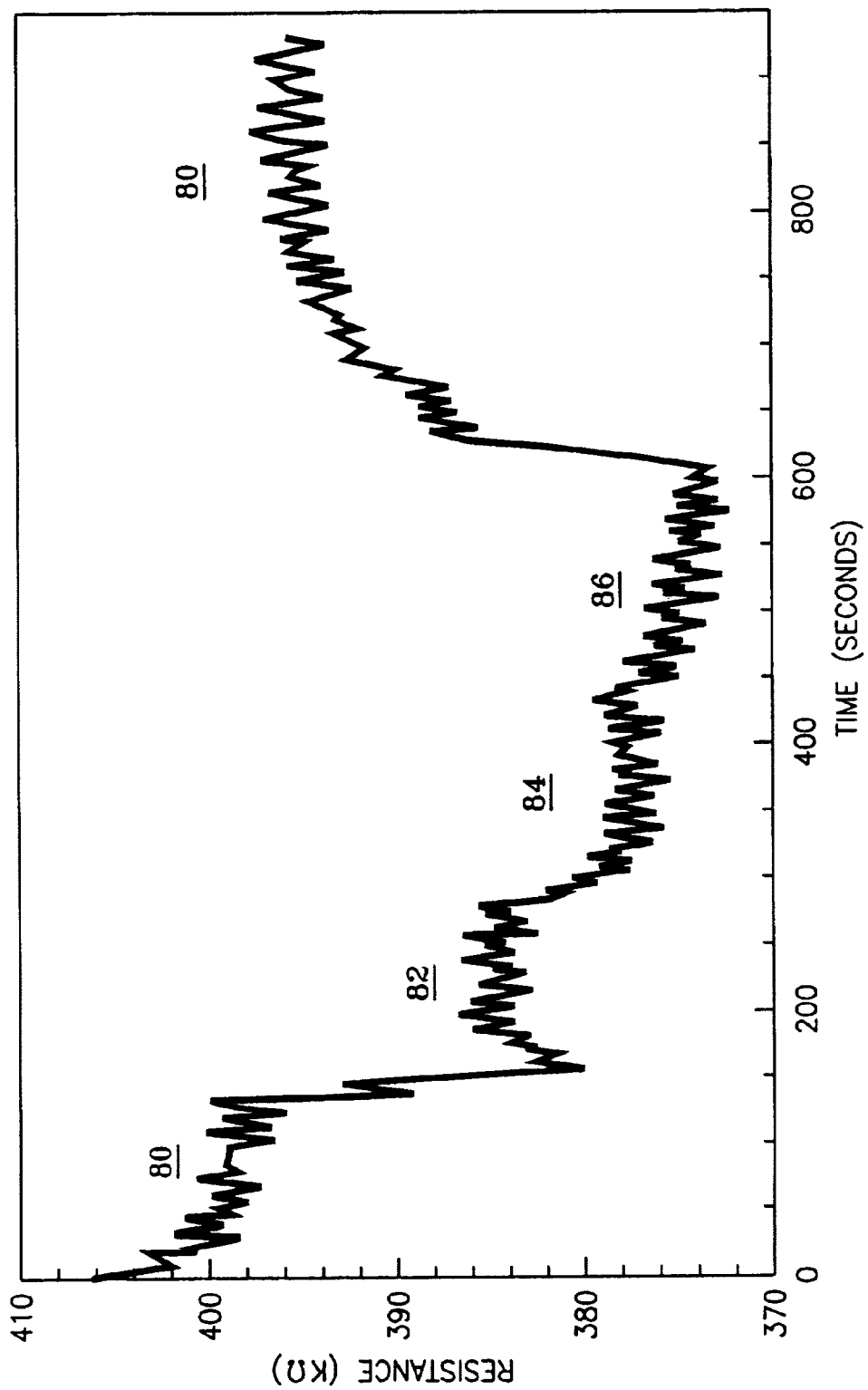
FIG. 8 shows the detection of different CO levels in a $H_2/N_2$ atmosphere at 50° C. (samples produced by Method 2).

Sensors Prepared by Method 2 (CuCl/Acetonitrile Solvent Evaporation). The CO sensing performance of a CuCl film sample prepared by Method 2 (direct precipitation of CuCl by evaporation of acetonitrile solutions) was evaluated in a $H_2/N_2$ atmosphere. Before testing, the sample was reduced in hydrogen for two hours at 150° C. This sample exhibited, a very strong and repeatable on/off response to carbon monoxide at 50° C., as shown in FIG. 7. FIG. 7 shows the CO sensitivity of CuCl film sample of Method 2 at 50° C. in the presence of $H_2$. The resistance of a sensor was tracked through periods of $N_2/H_2$ (0-ppm CO) 70 interrupted by periods of 1000-ppm CO gas 72. The resistance decreased in the presence of CO and then increased (returning to baseline) upon nitrogen/hydrogen purge. During sensor testing, the hydrogen content was varied between 25 and 75 vol %, and there was no change in the baseline resistance. Further, this sensor was able to detect CO over the range of 500 to 1500 ppm, as shown in FIG. 8. FIG. 8 illustrates the detection of different levels of CO in a $N_2/H_2$ atmosphere at 50° C. using a sensor of Method 2. The resistance of the sensor during periods of $N_2/H_2$ 80 is higher than the resistance when 500 ppm of CO gas 82 is introduced. Further, the resistance dropped again when the CO gas was increased to 1000-ppm 84. The resistance dropped for a third time as the CO gas was increased to 1500-ppm 86. The response of this sample to CO was reproducible over many cycles, without exhibiting any signs of degradation.

Figure 9:
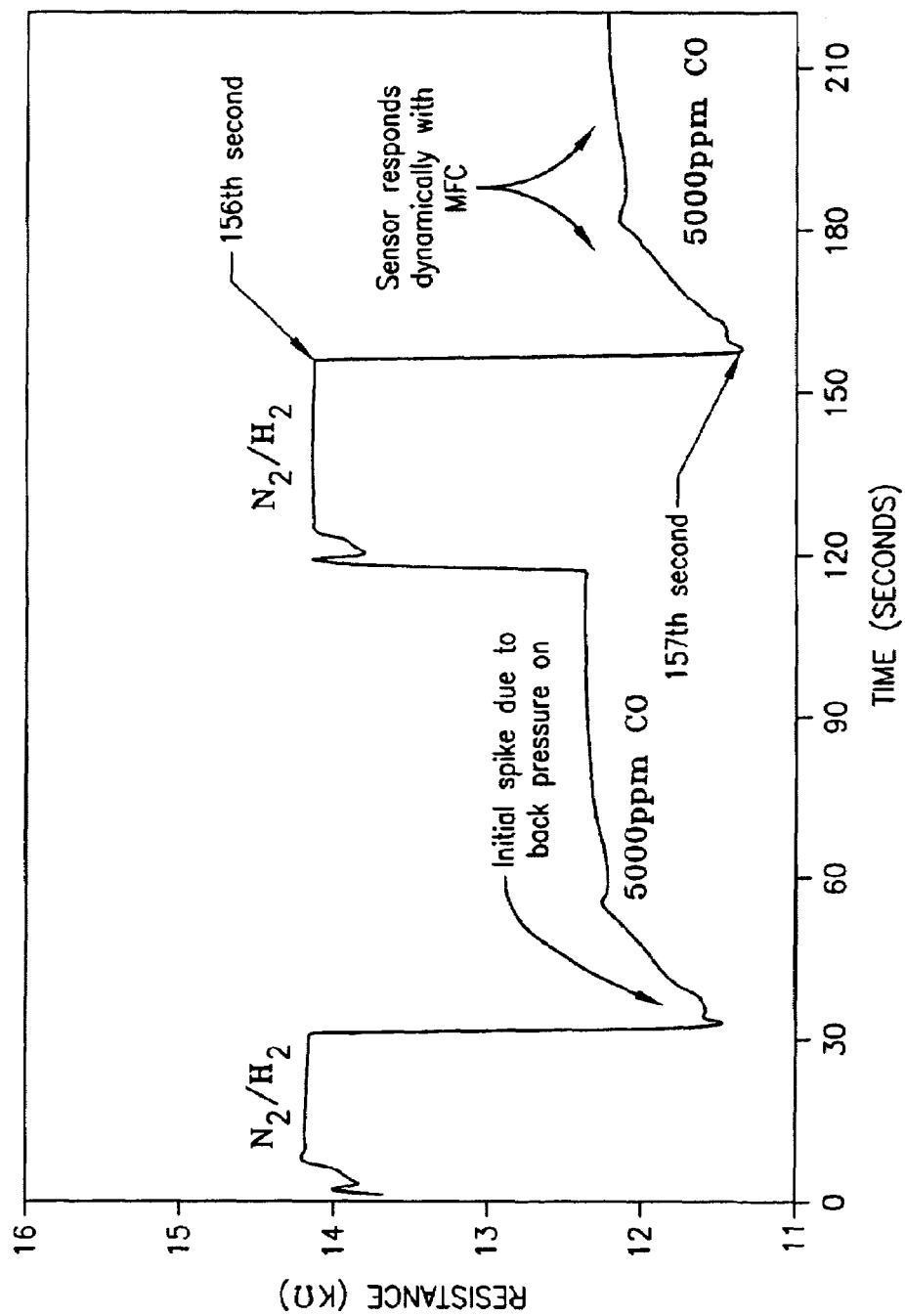
FIG. 9 illustrates the response time of a metal halide sensor manufactured by a thick film deposition technique.

FIG. 9 shows the CO sensitivity of a metal halide sensor manufactured by a thick film deposition technique described above. The resistance of the sensor was tracked through periods of $H_2/N_2$, interrupted by periods of 5000-ppm carbon monoxide gas. The sensor exhibited extremely fast response times, of about one second, in the presence of CO.

While we have shown that active CO sensors can be produced using chemical deposition methods, multiple deposition techniques would also be viable for producing CO sensors of the present invention, i.e. using metal halide based materials. Multiple deposition techniques include: pellet pressing, spin-coating, dip-coating, tape-casting, screen printing, radio-frequency (R.F.) sputtering, direct-current (D.C.) sputtering, reactive magnetron sputtering, and chemical vapor deposition (CVD) methods among others.

The above results indicate that the electrical resistance of certain copper chloride films can be very sensitive to carbon monoxide and insensitive to hydrogen, and that rapid responses are indeed possible. These are critical criteria for any CO sensing approach for automotive fuel cell applications. The results obtained also showed the importance of film fabrication methods on the electrical resistance and CO sensing performance of CuCl films. Baseline electrical resistance values of CuCl films varied over three orders of magnitude, depending on the film fabrication method. Further, the presence of (and the longevity of) measurable resistive responses to CO also varied with fabrication method.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims, which are incorporated herein by reference.

What is claimed is:

1. A sensor for determining a concentration of carbon monoxide in a reducing gas stream as a function of a measured electrical property, said sensor comprising:
   a. a substrate, said substrate having at least a first side and a second side, said substrate being non-conductive;
   b. a first electrode, said first electrode deposited on said first side of said substrate, said first electrode adapted to conduct electricity;
   c. a second electrode, said second electrode deposited on said first side of said substrate so as to not contact said first electrode, said second electrode adapted to conduct electricity; and
   d. a sensing material, said sensing material in electrical contact with said first electrode and said second electrode, said sensing material comprising a majority of cuprous chloride (CuCl), said sensing material capable of selectively adsorbing carbon monoxide from said reducing gas stream, said sensing material having an electrical property that varies in relation to said adsorbed carbon monoxide on said sensing material.

2. A sensor according to claim 1 wherein said substrate is alumina.

3. A sensor according to claim 1 wherein said first electrode is an interdigital electrode.

4. A sensor according to claim 1 wherein said second electrode is an interdigital electrode.

5. A sensor according to claim 1 wherein said sensing material comprises a minority of a copper halide wherein said copper of said copper halide has a valence of at least +2.

6. A sensor according to claim 1 further comprising a heater deposited on said second side of said substrate, said heater adapted to maintain said sensor at a substantially constant temperature.

7. A sensor according to claim 6 wherein said heater is a thick-film platinum heater deposited on said second side of said substrate.

8. A sensor according to claim 1 wherein said electrical property is selected from the group consisting of: resistance, impedance, capacitance, inductance, conductance, voltage and current.

9. The sensor according to claim 1 wherein said sensing material has a lamellar structure.

10. The sensor according to claim 1 wherein said lamellar structure comprises laminae of spherical crystals.

11. A method for using a sensor to determine a concentration of carbon monoxide in a reducing gas stream, said method comprising the steps of:
   a. passing said reducing gas stream to a sensor, said reducing gas stream being reducing in nature and containing CO and $H_2$, said sensor comprising:
      i. a substrate, said substrate having at least a first side and a second side, said substrate being non-conductive;
      ii. a first electrode, said first electrode deposited on said first side of said substrate, said first electrode adapted to conduct electricity;
      iii. a second electrode, said second electrode deposited on said first side of said substrate so as not to contact said first electrode, said second electrode adapted to conduct electricity; and
      iv. a sensing material in electrical contact with said first electrode and said second electrode, said sensing material comprising a majority of cuprous chloride (CuCl), said sensing material capable of selectively adsorbing carbon monoxide from said reducing gas stream, said sensing material having an electrical property that varies in dependence upon said adsorbed carbon monoxide on said sensing material;
   b. impressing a potential across said first electrode and said second electrode;

c. measuring said electrical property of said sensing material; and
d. outputting said measured electrical property to a device.

12. The method according to claim 11 wherein said device is a display device adapted to provide a read-out of said carbon monoxide concentration based upon said measured resistance.

13. The method according to claim 11 wherein said device is a controller adapted to adjust said gas stream in response to said output measurement.

14. The method according to claim 11 wherein said electrical property is selected from the group consisting of: resistance, impedance, capacitance, inductance, conductance, voltage and current.

15. A method for sensing a concentration of carbon monoxide while converting a hydrocarbon fuel into a reducing gas stream, said method comprising the steps of:
   a. reacting a flow of gases to produce a gaseous mixture of hydrogen ($H_2$), carbon dioxide ($CO_2$), carbon monoxide (CO), nitrogen ($N_2$), and water ($H_2O$);
   b. directing said gaseous mixture to at least a first reactor, said at least first reactor adapted to reduce carbon monoxide content and increase said hydrogen content, thereby forming a flow of reformate gas;
   c. directing said reformate gas to at least a second reactor, said at least second reactor adapted to combine a flow of air with said flow of reformate gas so as to oxidize said carbon monoxide to carbon dioxide and so as to not oxidize said hydrogen to water;
   d. directing said flow of air and reformate gas to a sensor, said sensor comprising:
      i. a substrate, said substrate having at least a first side and a second side, said substrate being non-conductive;
      ii. a first electrode, said first electrode deposited on said first side of said substrate, said first electrode adapted to conduct electricity;
      iii. a second electrode, said second electrode deposited on said first side of said substrate so as not to contact said first electrode, said second electrode adapted to conduct electricity; and
      iv. a sensing material in electrical contact with said first electrode and said second electrode, said sensing material comprising a majority of cuprous chloride (CuCl), said sensing material capable of selectively adsorbing carbon monoxide from said flow of air and reformate gas, said sensing material having an electrical property that varies in dependence upon said adsorbing carbon monoxide on said sensing material; and
   e. providing feedback to said at least second reactor, said at least second reactor further adapted to adjust said flow of air in response to said measured concentration of said carbon monoxide.

16. A method according to claim 15 further comprising the step of: diverting said oxidized flow of air and reformate gas from said next device when said concentration of carbon monoxide detected by said sensor exceeds a threshold.

17. A method according to claim 16 wherein said next device is chosen from the group consisting of: PEM fuel cell and storage tank.

18. A method according to claim 15 further comprising the step of: directing said oxidized flow of air and reformate gas to a next device.

19. A method according to claim 18 wherein said next device is chosen from the group consisting of: PEM fuel cell and storage tank.

20. A method according to claim 15 wherein said electrical property is selected from the group consisting of: resistance, impedance, capacitance, inductance, conductance, voltage and current.

21. A sensor that can selectively detect a concentration of carbon monoxide in a hydrogen-containing gas stream devoid of oxygen, said sensor comprising a sensing material having a lamellar structure, wherein a majority of said sensing material is cuprous chloride (CuCl).

22. A sensor according to claim 21, wherein said concentration of carbon monoxide is between about 10 to about 2000 part per million.

23. A sensor according to claim 21, wherein said hydrogen-containing gas stream is a reformed fuel gas stream.

24. A sensor according to claim 23, wherein said reformed fuel gas stream comprises carbon monoxide, carbon dioxide, hydrogen and nitrogen.

25. A sensor for selectively measuring a concentration of carbon monoxide in a hydrogen-containing gas stream devoid of oxygen, where said sensor comprises a sensing material comprising a majority of cuprous chloride (CuCl) that undergoes a reversible change in at least one electrical property only when carbon monoxide is present.

26. A sensor according to claim 25, wherein said at least one electrical property is resistance, impedance, capacitance, inductance, conductance, voltage or current.

27. A sensor according to claim 25 operated at a temperature to promote said reversible change in said at least one electrical property of said cuprous chloride.

28. A system for determining a concentration of carbon monoxide in a gas stream as a function of a measured electrical property, said system comprising:
   a. a conduit, said conduit containing a flow of reducing gas, wherein said reducing gas comprises said carbon monoxide; and
   b. a sensor disposed in said conduit, said sensor comprising:
      i. a first electrode adapted to conduct electricity;
      ii. a second electrode adapted to conduct electricity, wherein said first electrode and said second electrode do not physically contact one another; and
      iii. a sensing material, said sensing material in electrical contact with said first electrode and said second electrode, said sensing material comprising a majority of cuprous chloride (CuCl), said sensing material capable of selectively adsorbing said carbon monoxide from said flow of reducing gas, said sensing material having an electrical property that varies in relation to said adsorbing carbon monoxide on said sensing material.

29. A sensor for determining a concentration of carbon monoxide in a reducing gas stream as a function of a measured electrical property, said sensor comprising:
   a. a substrate, said substrate having at least a first side and a second side, said substrate being non-conductive;
   b. a first electrode, said first electrode deposited on said first side of said substrate, said first electrode adapted to conduct electricity;
   c. a second electrode, said second electrode deposited on said first side of said substrate so as to not contact said first electrode, said second electrode adapted to conduct electricity; and
   d. a sensing material, said sensing material in electrical contact with said first electrode and said second electrode, said sensing material comprising a majority of a metal halide having a lamellar structure, said sensing material capable of selectively adsorbing carbon monoxide from said reducing gas stream, said sensing material having an electrical property that varies in relation to said adsorbed carbon monoxide on said sensing material.

30. The sensor according to claim 29 wherein said metal halide is cuprous chloride (CuCl).

31. The sensor according to claim 29 wherein said lamellar structure comprises laminae of spherical crystals.

32. The sensor according to claim 29 wherein said sensing material additionally comprises a minority of a copper halide, wherein said copper of said copper halide has a valence of at least +2.

* * * * *

UNITED STATES PATENT AND TRADEMARK OFFICE
CERTIFICATE OF CORRECTION

PATENT NO. : 6,985,082 B1
DATED : January 10, 2006
INVENTOR(S) : Dutta et al.

It is certified that error appears in the above-identified patent and that said Letters Patent is hereby corrected as shown below:

Column 5,
Line 15, delete "opera ting" and insert -- operating --.

Column 6,
Line 3, delete "acetdnitrile" and insert -- acetonitrile --.

Signed and Sealed this

Twenty-eighth Day of March, 2006

JON W. DUDAS
*Director of the United States Patent and Trademark Office*

UNITED STATES PATENT AND TRADEMARK OFFICE
CERTIFICATE OF CORRECTION

PATENT NO.        : 6,985,082 B1
APPLICATION NO.   : 09/903916
DATED             : January 10, 2006
INVENTOR(S)       : Dutta et al.

Page 1 of 1

It is certified that error appears in the above-identified patent and that said Letters Patent is hereby corrected as shown below:

In the Specification

Column 1, Line 3, In the first paragraph please delete:
"The present invention was made with Government support under Grant No. DE-FG02-99ER 86099 awarded by the U.S. Department of Energy. The United States Government may have certain rights to this invention under 35 U.S.C. § et seq."

Please add:
"STATEMENT REGARDING FEDERALLY SPONSORED RESEARCH OR DEVELOPMENT
This invention was made with government support under DE-FG02-99ER86099 awarded by the Department of Energy. The government has certain rights in the invention."

Signed and Sealed this
Eighteenth Day of August, 2020

Andrei Iancu
*Director of the United States Patent and Trademark Office*